US008911995B2

(12) United States Patent
Ammer et al.

(10) Patent No.: US 8,911,995 B2
(45) Date of Patent: Dec. 16, 2014

(54) CULTURE SYSTEM AND METHOD FOR IMMUNOGENICITY AND IMMUNOFUNCTION TESTING IN VITRO

(75) Inventors: Richard Ammer, Grenoble (FR); Christian Demmler, Berlin (DE); Uwe Marx, Spreenhagen (DE); Annika Lubitz, Berlin (DE); Michael Sacharjat, Berlin (DE); Christoph Giese, Berlin (DE)

(73) Assignee: ProBioGen AG, Berlin (DE)

( * ) Notice: Subject to any disclaimer, the term of this patent is extended or adjusted under 35 U.S.C. 154(b) by 933 days.

(21) Appl. No.: 12/673,154

(22) PCT Filed: Aug. 21, 2008
(Under 37 CFR 1.47)

(86) PCT No.: PCT/EP2008/060937
§ 371 (c)(1),
(2), (4) Date: Apr. 13, 2011

(87) PCT Pub. No.: WO2009/024595
PCT Pub. Date: Feb. 26, 2009

(65) Prior Publication Data
US 2011/0312512 A1 Dec. 22, 2011

Related U.S. Application Data

(60) Provisional application No. 60/957,212, filed on Aug. 22, 2007.

(51) Int. Cl.
| *C12N 5/00* | (2006.01) |
| *C12M 1/32* | (2006.01) |
| *C12M 1/12* | (2006.01) |
| *C12M 1/42* | (2006.01) |

(52) U.S. Cl.
CPC ............... *C12M 25/14* (2013.01); *C12M 23/12* (2013.01); *C12M 35/08* (2013.01)
USPC .......................................... 435/397; 435/325

(58) Field of Classification Search
USPC .................................................. 435/397, 325
See application file for complete search history.

(56) References Cited

U.S. PATENT DOCUMENTS

| 4,835,102 | A * | 5/1989 | Bell et al. .................. 435/29 |
| 6,248,721 | B1 | 6/2001 | Chang |
| 6,939,546 | B2 | 9/2005 | Nauss et al. |
| 7,763,456 | B2 * | 7/2010 | Li et al. ................... 435/288.5 |
| 2003/0152550 | A1 | 8/2003 | Granucci et al. |
| 2004/0180386 | A1 | 9/2004 | Carr et al. |
| 2005/0142530 | A1 | 6/2005 | Galavotti |
| 2005/0260745 | A1 * | 11/2005 | Domansky et al. ........ 435/294.1 |
| 2006/0110822 | A1 | 5/2006 | Robbins et al. |
| 2006/0270029 | A1 | 11/2006 | Warren et al. |
| 2007/0037277 | A1 | 2/2007 | Shuler et al. |

FOREIGN PATENT DOCUMENTS

| CN | 1812838 A | 8/2006 |
| JP | 2007-075094 | 3/2007 |
| JP | 2004-147555 | 5/2007 |
| WO | WO 02/072423 A1 | 9/2002 |
| WO | WO 02/102830 A1 | 12/2002 |
| WO | WO 03/061585 A2 | 7/2003 |
| WO | WO 03/104439 A2 | 12/2003 |
| WO | WO 2004/065616 A2 | 8/2004 |
| WO | WO 2005/104755 A2 | 11/2005 |
| WO | WO 2006/056769 A1 | 6/2006 |

OTHER PUBLICATIONS

Search Report issued in related Chinese Patent Application No. 200880103929, dated Sep. 7, 2012.
European Communication issued in related European Patent Application No. 08787381.6, dated Jan. 30, 2013.
International Search Report for PCT/EP2008/060937 completed Jun. 14, 2010.
Written Opinion of the International Searching Authority for PCT/EP2008/060937 completed Jun. 14, 2010.
Griffith et al., "Capturing Complex 3D Tissue Physiology in vitro," *Mol. Cell Biol.*, vol. 7, pp. 211-224 (2006).
Schellekens, "Bioequivalence and the Immunogenicity of Biopharmaceuticals," *Drug Discovery*, vol. 1, pp. 457-462 (2002).
European Communication issued in related European Patent Application No. 08787381.6, dated Aug. 14, 2013.

* cited by examiner

*Primary Examiner* — Karen Cochrane Carlson
*Assistant Examiner* — Natalie Moss
(74) *Attorney, Agent, or Firm* — Foley & Lardner LLP

(57) ABSTRACT

The invention provides a culture device comprising a plurality of culture units, wherein each unit comprises a culture chamber, an inlet port for liquid supply of the culture and an outlet port for discharging liquid from the unit, wherein the inlet port is in fluid communication with the culture chamber and the culture chamber is in fluid communication with the outlet port for allowing a liquid flow through the culture chamber. The culture device is particularly suitable for testing immune cells and immunofunction in vitro. Aspects of the invention include a culture device and associated methods for cultivating immune cells and an in vitro method of analysing the effect of a test compound on immune cells.

17 Claims, 6 Drawing Sheets

Figure 1
Figure 1A
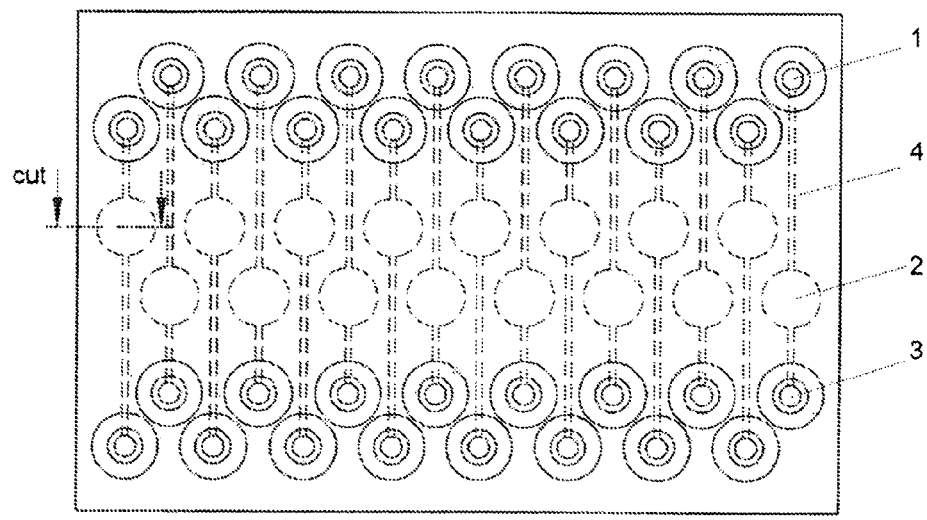
Figure 1B
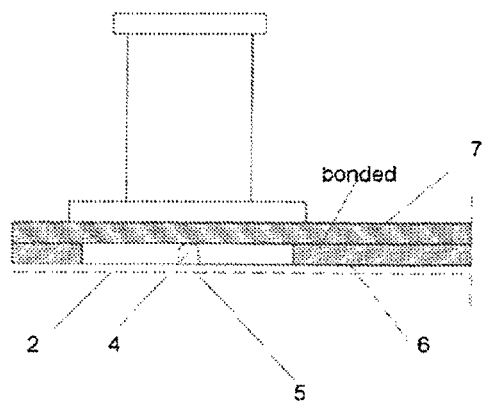

Figure 2A
Figure 2
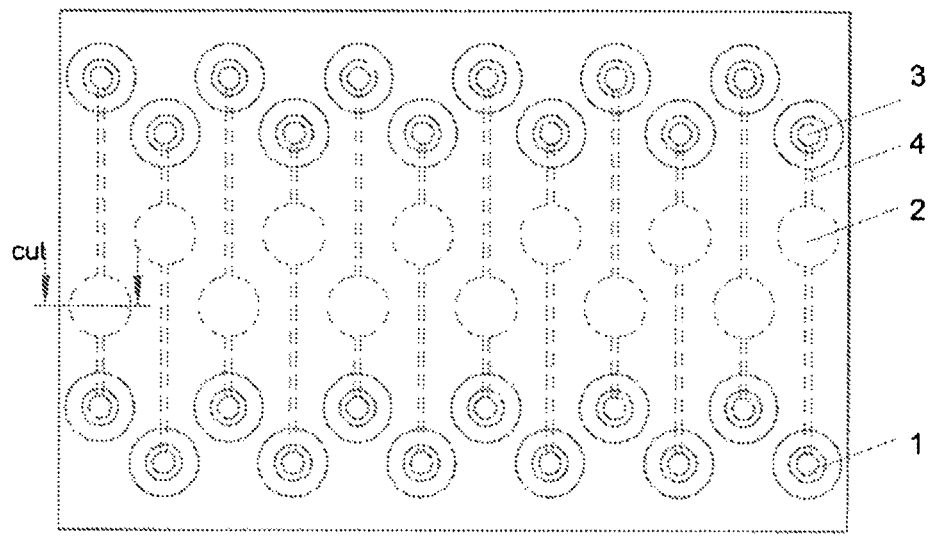
Figure 2B
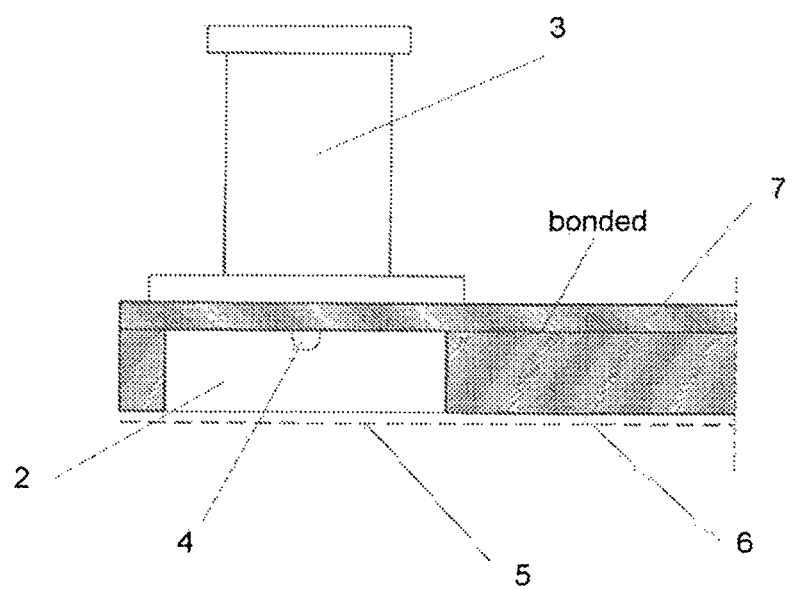

Figure 3
Figure 3A
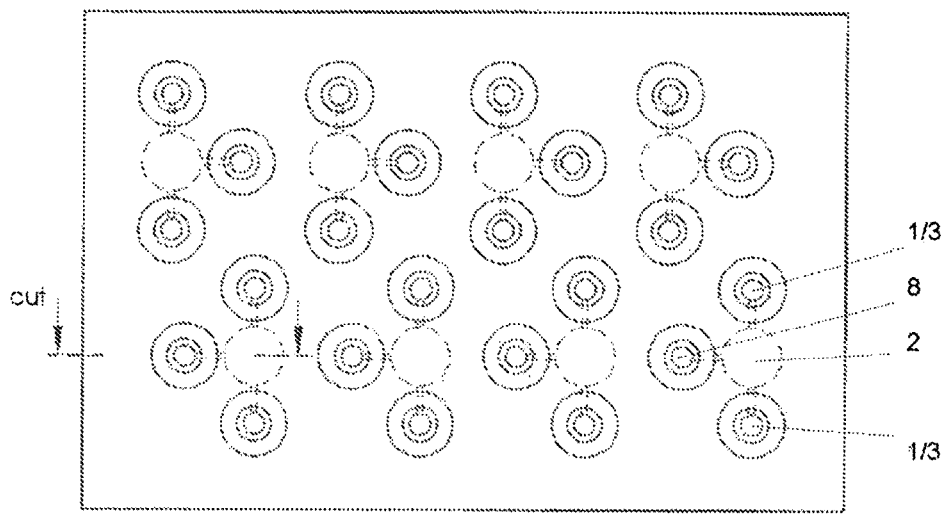
Figure 3B
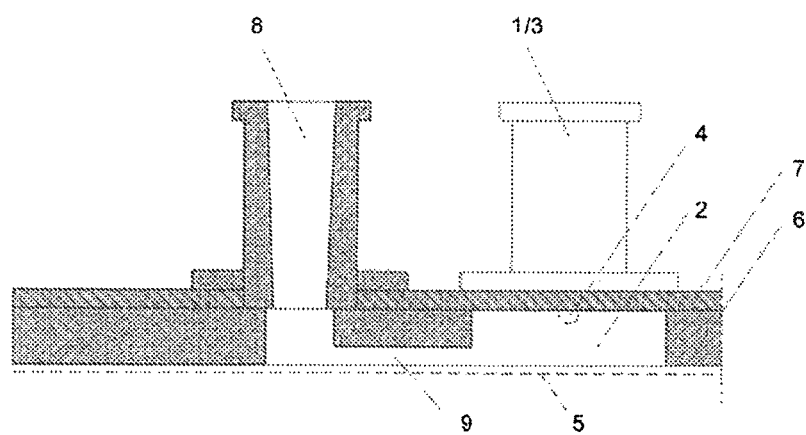

Figure 4
Figure 4A
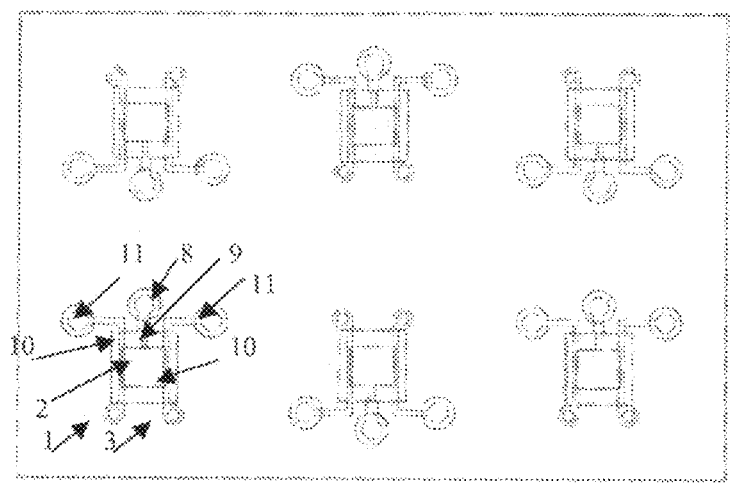
Figure 4B
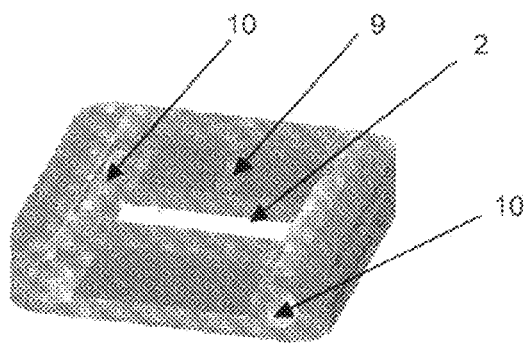

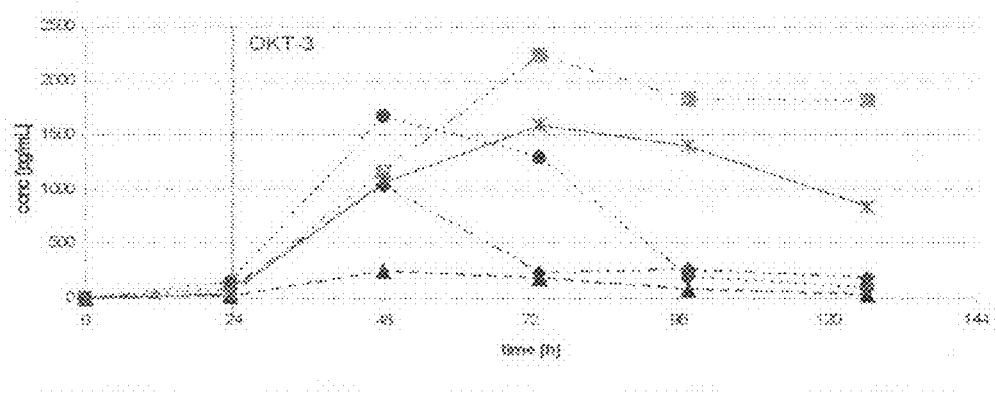
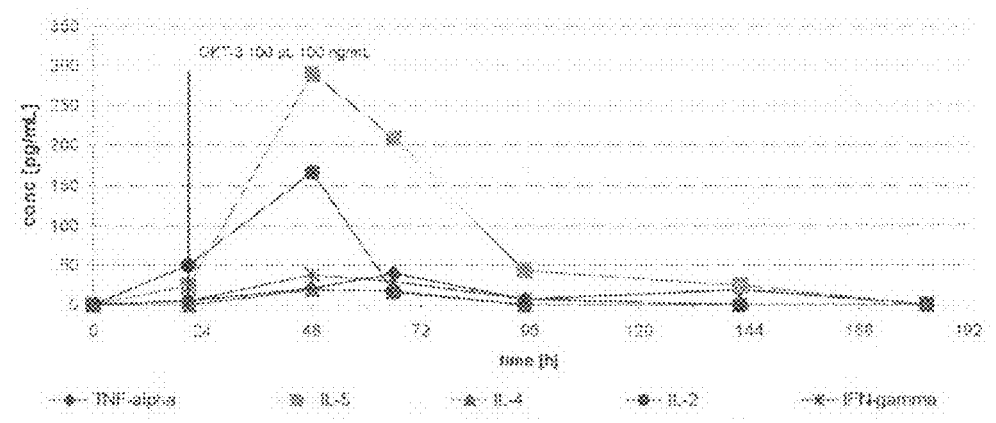
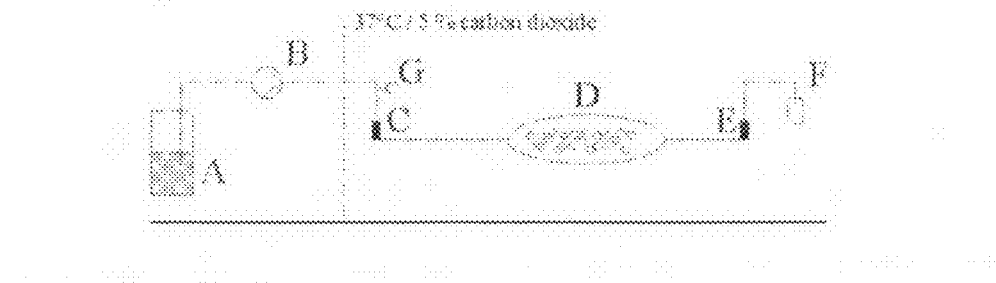

CULTURE SYSTEM AND METHOD FOR IMMUNOGENICITY AND IMMUNOFUNCTION TESTING IN VITRO

CROSS-REFERENCE TO RELATED APPLICATIONS

This application is the U.S. National Phase of International Patent Application No. PCT/EP2008/060937, filed on Aug. 21, 2008, which claims the benefit of priority from U.S. Provisional Patent Application No. 60/957,212, filed Aug. 22, 2007. The Contents of these applications are incorporated herein by reference in their entirety.

FIELD OF THE INVENTION

The invention relates to a culture device and a method of culturing eukaryotic cells, notably immune cells. The invention further relates to a method of analysing the effect of a test compound on immune cells in vitro.

BACKGROUND OF THE INVENTION

In early preclinical drug development, it is necessary to carry out comparative analyses of the effect of substances on cells in vitro. For this purpose, cell cultures need to be prepared under strictly controlled conditions and treated with the therapeutic agent of interest. Reliable results can only be obtained, if individual (i.e. identical or different) cell cultures are tested in a reproducible and highly comparable manner.

But, often serious problems are encountered. For example, cell cultures are damaged or put under stress during the cell culture preparation or testing procedures, and thus, the analysis may show results that are at least in part a consequence of such damage. Moreover, applying conclusions drawn from results obtained on damaged cells to the situation in vivo may cause fatal errors. Furthermore, the damages or stressful conditions are not reproducible between individual cell cultures and may influence a variety of factors, potentially leading to a high percentage of false positives or false negatives.

For this reason, in vivo tests in animal model systems subsequent to in vitro tests are very important. This leads to the paradox that the validity expected for experiments in human cell culture themselves cannot be realized due to uncontrolled testing conditions. The expected validity is foiled by experimental artefacts.

On the other hand, in vivo results obtained by animal studies are less afflicted by experimental artefacts. However, they have per se only limited validity for human applications (not to mention the problem of breeding genetically identical animal cohorts for comparative analysis).

For this reason, efforts have been made, e.g., by starting highly expensive genome and proteome projects, to assure the transferability of results from animals to humans. However, a satisfying solution to this problem is still far from being achieved.

Therefore, at present the risk of new pharmaceutical developments still largely pertains to the field of clinical studies, which is the most expensive and ethically most problematic field. Similar problems also exist in the development of diagnostic tests on cell cultures.

The invention thus seeks to develop a culture device and methods for testing in vitro that minimize stressful conditions on the living cell material. This will permit to increase the validity of results obtained by comparative analyses, and preferably, these may be directly extrapolated to the whole organism that corresponds to the cultured cells. Thereby, it may be possible to avoid or reduce the number of further animal tests.

All the components of cosmetics, pharmaceutical drugs and chemical consumer products require testing for a broad spectrum of side effects. The ultimate goal of the risk assessment strategy is to define the use and application of the product to minimize health and environmental hazards. In addition to, e.g., toxic, corrosive, carcinogenic effects and embryo toxicity, immunogenicity has to be taken into account for product safety. Product-related immunogenicity may cause, e.g., skin sensitization, allergy and anaphylaxis.

Immunogenicity is only desirable for the purpose of vaccination. Pharmaceutical drugs, cosmetic products and other consumer-related chemicals including food ingredients, as well as combinations thereof may cause unexpected immunogenicity when applied to the human body. Thus, immunogenicity and altered immunofunction is a fundamental problem associated with the use of chemicals and biopharmaceuticals.

Product-related parameters such as drug design, manufacturing process, formulation or route of administration may have an influence on immunogenicity (Schellekens, H., Bioequivalence and the Immunogenicity of Biopharmaceuticals. Nature Reviews Immunology. Vol. 1, 457; 2002).

New chemical entities, but also biopharmaceutical drugs such as recombinant proteins, animal- and plant-derived components may cause the generation of neutralizing antibodies, allergic reactions and anaphylaxis in the patient. New chemical entities, but also biological substances, such as antibodies or cytokines react and interfere highly specifically with a certain target, or have certain species specificity in their mode of action.

Therefore, for testing immunogenicity and immunofunction, model systems need to be developed that closely mimic the situation in humans. Thus, in order to study these effects, equivalent test systems and robust procedures based on human immune competent lymphatic organoids are needed.

A number of in vitro tests using human cells are available, but they do not emulate organ- or tissue-functionality, and thus, are of limited value. Therefore, for the investigation of drug efficacy and adverse effects, in vivo tests using animal species have been absolutely necessary.

A large panel of validated animal testing systems are established and mandatory for product approval, especially in the field of pharmaceuticals, chemical and cosmetic industry.

For early pre-clinical studies as well as late drug screening procedures, a number of transgenic animal models have been developed and are already available for testing of induction of immune responses. Well-established animal models are mandatory for late pre-clinical toxicity testing (e.g. mice, rat, dog and non-human primates). Within the scope of a clinical trial, immunogenicity testing in humans is focussing on the analysis of blood and urine samples of treated volunteers for drug-neutralising antibodies.

Humanized animal models have been described in, e.g., WO 2006/056769 A1, providing mice transgenic for human MHC class II. WO 02/102830 A1 describes animal models, which supplement or replace the natural albumin sequence with a typical human serum albumin sequence. U.S. Pat. No. 6,248,721 provides humanized animal models for the evaluation of vaccines designed to confer immunity against human pathogens, including vaccines directed against the human immunodeficiency virus.

Other approaches have aimed at the identification of T cell epitopes. US 2004/0180386 A1 describes a method for epitope mapping (screening) using peptide libraries of overlapping sequences to design new proteins with reduced immunogenicity.

Moreover, a number of data libraries based on computational models have been generated in order to estimate the probability of antigen matching to known human relevant epitopes. For example, U.S. Pat. No. 6,939,546 B2 describes a computer-based model for binding studies of peptides to Class II MHC-receptors. Some predictive information about the immunogenic potential of peptides can be generated. These data can help to reduce the number of in vitro tests that need to be done subsequently.

Methods have been described for testing immune functions with the help of isolated animal and human cells. Mostly isolated peripheral blood mononuclear cells (PBMC) of different species are cultured in suspension and exposed to drugs in different concentrations. Induced cell proliferation and cytokine release is monitored over a short period of, e.g., 1 to 48 hours.

For a more detailed investigation, defined subpopulations of PBMC are used for the analysis of cell-type specific responses. T cells, for example, are used for peptide and epitope mapping and dendritic cells are used to analyse the presentation of antigens. US 2003/0152550 A1 describes the use of dendritic cells in screening and testing of drugs affecting dendritic cell maturation.

Common read-out parameters are antigen-dependent proliferation of primed lymphocytes and antigen-dependent cytokine secretion.

A major drawback of existing in vitro tests is that they are carried out on a suspension of cells in a test tube, whereas most of the physiological reaction in the body is tissue-related and organ-related. Secondary lymphatic organs and all solid body tissues like skin are the structural and environmental basis for most of the immune reactions and not the peripheral blood. Therefore, artificial tissue models which emulate tissue or organ functionality are needed.

Bioartificial organs have been developed for the purpose of fluid processing (US 20050142530). Other systems have aimed at providing tissue-engineered systems (comprising liver tissue, kidney tissue, cardiac tissue, cartilage tissue, or bone marrow tissue) for testing drug metabolism and toxicity (WO 2004065616 A2, WO2003104439 A2). US20060110822 describes a multiwell-based perfusion flow bioreactor for drug testing on cells in dynamic cell cultures.

For suitable tissue culture techniques, it has become obvious that, in addition to efficient oxygen and nutrient supply, the establishment of local gradients of (i) metabolites, (ii) cytokines, and (iii) chemokines and other (undiscovered) parameters, as well as structured surfaces for chemotaxis and local settlement (including intercellular cross-talk via tight junctions), are crucial prerequisites for the proper emulation of in vivo environments (Griffith, L. G. and Swartz, M. A. 2006. Capturing complex 3D tissue physiology in vitro. Nat Reviews Molecular Cell Biology, 7: 211-224). This provoked a shift from the development of homogeneous culture systems to heterogeneous ones and an emphasis on controlled, continuously adjustable, long-term culture processes.

The basic aims of those cell culture devices and process developments are to create an architecture and homeostasis mimicking the specific relevant human microenvironment for self-organisation of a specific tissue (see US 2005/0142530 A1).

Human tissue based models that emulate immune organ function are conceived to bridge the gap between early lead optimization and the pre-clinical development stage. Human or animal lymphatic organoid models may provide insights into the mode of drug action and, in addition, can be used to refine a product related risk profile.

A technological platform for the emulation of human immune function in vitro using human cells in a tissue-like (organoid) arrangement and robust testing procedures give the opportunity for predictive in vitro testing of immunogenicity and human immune functionality. It can be used for optimised product development and better patient and consumer health and safety. In addition, the technology and procedures give the chance for reduction and replacement of animal testing.

Attempts have been made to simulate the vaccination process in vitro in order to investigate vaccine candidates for their mode of action and their potency. For this purpose, a modular miniaturized immunobioreactor system (WO 2005/104755 A2) has been developed, which comprises a lymphoid tissue equivalent. The lymphoid tissue equivalent is created by seeding T and B cells onto microcarriers, and cocultivating T and B cell populated microcarriers in a porous container.

In the prior art, most of methods for tissue engineering are based on adherent cells. Cell culture methods for non-adherent cells normally use suspension cultures. A disadvantage of suspension culture is that cells in suspension culture are single cells that do not emulate tissue or organ functionality. Suspension cultures further suffer from the problem that it is difficult to withdraw samples without removing suspended cells from the culture, without using tedious procedures such as centrifugation and without interrupting the incubation. Therefore a cell culture system for non-adherent cells having the advantages of cell culture systems for adherent cells would be very desirable.

In general, interruption of the incubation of cells exerts stress on the cells, which may bear the risk of measuring artefacts due to such stress. Therefore, for comparative analysis, a culture method allowing to analyse the effect of a test compound on cells without interrupting the incubation of cells is needed.

SUMMARY OF THE INVENTION

The above-mentioned problems are solved by the invention, which provides a cell culture device and a method for testing immunogenicity and immunofunction in vitro. The culture devices and methods of the invention may provide a microenvironment. The microenvironment allows comparable cellular responses to those in vivo.

In one aspect, the invention provides a culture device having a top side, a bottom side, and at least one lateral side, comprising a plurality of culture units, wherein each unit comprises
  (i) a culture chamber,
  (ii) an inlet port for reversibly connecting the unit with an external liquid supply and
  (iii) an outlet port for discharging liquid from the unit,
    wherein the inlet port is in fluid communication with the culture chamber and the culture chamber is in fluid communication with the outlet port for allowing a liquid flow through the culture chamber,
    wherein the inlet port is accessible for connecting an external liquid supply from the top side or lateral side of the culture device, and the outlet port is accessible for connecting a discharge conduct from the top side or lateral side of the device.

In a further aspect the invention provides a culture device, comprising a plurality of culture units, wherein each unit comprises (i) a culture chamber,
(ii) an inlet port for reversibly connecting the unit with an external liquid supply and
(iii) an outlet port for discharging liquid from the unit, wherein the inlet port is in fluid communication with the culture chamber and the culture chamber is in fluid communication with the outlet port for allowing a liquid flow through the culture chamber, whereby the mainstream of the liquid flow traverses the culture chamber within the plane of the culture device.

According to the invention the fluid communication may be established by a channel between the culture chamber and the inlet port and a channel between the culture chamber and the outlet port.

The culture device may comprise a plurality of culture units for allowing multi-parallel incubation and testing of the cells. The culture units of the culture device may be in a miniaturized format, which allows to incorporate a high number of culture units into a single culture device. Thereby, several units may be handled on a single device, and may be, for example, exposed under purely identical conditions to a defined environment, e.g., temperature, gas and humidity.

Furthermore, medium to high-throughput applications may be realized with the culture device according to the invention. The culture device according to the invention may comprise 2 to 200 culture units.

In one embodiment, the culture chamber of the culture device has a culture volume from 25 to 1000 µl. In another embodiment the culture chamber of the culture device has a culture volume from 50 to 250 µl, preferably 50 to 150 µl.

Test substances and/or stimulatory agents may be added to living cell material in each individual unit separately.

The culture device may be manufactured as to allow microscopic inspection of cells present in the culture chambers.

The invention also provides a method of cultivating immune cells, comprising the steps of
(a) introducing a suspension of immune cells in an aqueous matrix-forming composition into a culture chamber,
(b) solidifying the suspension, thereby forming a matrix having the immune cells embedded therein, and
(c) incubating the immune cells at predefined culture conditions for a predefined period of time, whereby the matrix is continuously perfused with liquid culture media and supplements.

Furthermore, the invention provides a method of cultivating immune cells, comprising the steps of
(a) introducing a suspension of immune cells in an aqueous matrix-forming composition into the culture chamber of at least one culture unit of the culture device of the invention,
(b) solidifying the suspension, thereby forming a matrix having the immune cells embedded therein, and
(c) incubating the immune cells at predefined culture conditions for a predefined period of time, whereby the matrix is continuously perfused with liquid culture media and supplements.

In another aspect, a method of cultivating immune cells is provided, comprising incubating immune cells embedded in a matrix at predefined culture conditions for a predefined period of time, whereby the matrix is continuously perfused with liquid culture media and supplements.

Furthermore, the invention provides a method of cultivating immune cells, comprising incubating immune cells embedded in a matrix in the culture chamber of at least one culture unit of the culture device of the invention, at predefined culture conditions for a predefined period of time, whereby the matrix is continuously perfused with liquid culture media and supplements.

According to the invention, individual culture units may provide comparable conditions. As such, the conditions may be similar or essentially identical.

In a further aspect, the invention provides a method of analysing the effect of a test compound on immune cells, which comprises the steps of
(a) incubating immune cells embedded in a matrix in the culture chamber of at least one culture unit of the culture device of the invention, at predefined culture conditions for a predefined period of time, whereby the matrix is continuously perfused with liquid culture media and supplements,
(b) adding the test compound to at least one culture unit through the inlet port,
(c) incubating immune cells as described in step a) in the presence of the at least one test compound,
(d) removing at least one sample of the culture media discharged from the outlet port of the at least one culture unit to which the test compound was added, and
(e) analysing the sample for an effect of the test compound on the immune cells.

In another aspect, the method of analysing the effect of a test compound on immune cells may further comprise analysis of the immune cells by a method selected from the group of immune fluorescence, light microscopy, flow cytometry, fluorescence activated cell sorting, histology, and enzyme linked immuno-spot methods (ELISPOT) and others after the culture process.

BRIEF DESCRIPTION OF THE FIGURES

FIGS. 1 to 4 show engineering drawings (top views) of preferred embodiments of the device (devices 1 to 4, respectively) according to the invention. The FIGS. 1B, 2B and 3B show cross-sections through the culture compartment of the different embodiments of the device along the corresponding axis as illustrated in the drawing. FIG. 4B shows a 3D projection of a culture compartment according to device 4. This cassette comprising the culture compartment as well as the first and second hollow fibre membranes can be inserted into the baseplate of the culture device.

FIG. 5 shows the time dependent cytokine profile according to example 1. The experiment was performed using device 1 as illustrated in FIG. 1 but having a larger culture compartment of 160 µL.

FIG. 6 shows the time dependent cytokine profile according to example 2. The experiment was performed using device 1 as illustrated in FIG. 1 but having a larger culture compartment of 160 µL.

FIG. 7 exemplarily shows one culture unit (consisting of media channels and culture compartment) with the peripheral fluidic system.

DETAILED DESCRIPTION OF THE INVENTION

Definitions

Figure 8:
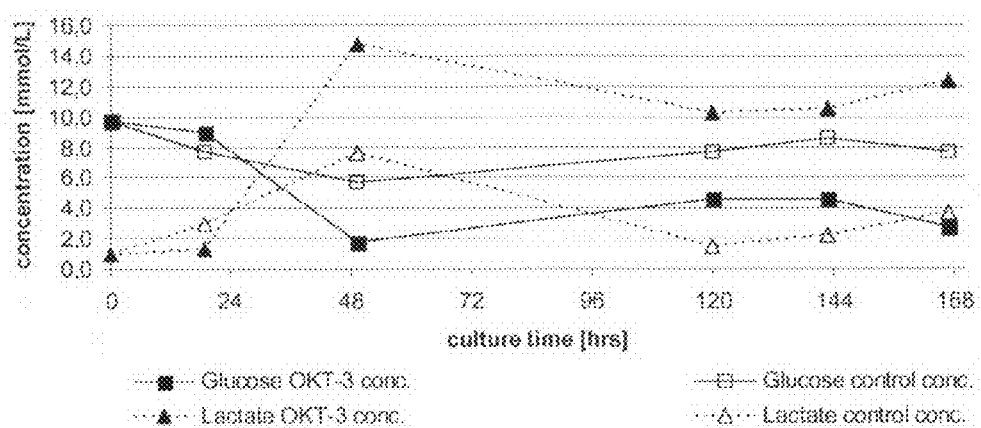
FIG. 8 shows a glucose and lactate profile of PBMC cultures in device 4 according to example 4. The data points indicate the concentration of these metabolic parameters in the flow through in a time dependent manner.

Autocrine factors are all those substances secreted by cells, which support and mediate maintenance, growth or differentiation of the same cell that secreted the factor.

Paracrine factors are all those substances secreted by a cell, which support and mediate maintenance, growth or differentiation of another but adjacent cell.

Self-conditioning describes all factors leading to improved cell behaviour.

Differentiation means the development of tissue-specific functions of cultured cells.

Maintenance describes the ability to keep all functions of a given tissue constant within a given cell culture process.

Living cell material describes viable primary cells, as well as cell lines, organoids or cell aggregates of human or animal origin.

Media stands for liquids with nutrients and substances necessary for cultivation of cells.

Supplements describe substances to be added to culture media in order to induce or modify cell function (e.g., cytokines, growth factors, serum).

Matrix describes substances or mixtures thereof for surface coating or voluminous application enhancing proliferation, differentiation and function or tissue formation of cells. Matrices can include artificial or biogenic substances like hydrogels, foams, sponges, fabrics or non-woven fibres. Matrices are defined by structure, chemical composition and/or functionalisation, e.g., with extra-cellular matrix proteins.

Microenvironment means local concentration of substances surrounding and influencing cells on a micrometer scale.

Perfusion means directed media and/or gas transport through the culture chamber.

Immunogenicity is the ability of a particular substance (antigen) to provoke an immune response. An immune response can be humoral and/or cell mediated.

Immunofunction comprises the ability of an organism to recognize the presence of pathogens and exogenous substances and to react accordingly (e.g., production of cytokines), which could trigger an immune response.

Cytokines are 8-30 kDa proteins and glycoproteins, which are produced by many cell types and operate as signals in cell-cell communication. They play a central role in the immune system and are involved in a variety of immunological, inflammatory and infectious diseases.

Chemokines are a family of small cytokines, which are able to induce directed chemotaxis in nearby responsive cells. These proteins exert their biological effects by interacting with G protein-linked transmembrane receptors called chemokine receptors, that are selectively found on the surfaces of their target cells.

Stimulators are drugs that stimulate the immune system by inducing activation, or increasing an activity of any of its components, e.g., increasing cell proliferation. One notable example includes granulocyte macrophage colony-stimulating factor, commercially available as "Leukine". There are two main categories of immunostimulators: Specific immunostimulators are those which provide antigenic specificity in immune response, such as vaccines or any antigen. Non-specific immunostimulators are those which act irrespective of antigenic specificity to augment immune response of other antigen or stimulate components of the immune system without antigenic specificity, such as adjuvants and non-specific immunostimulators.

Growth and differentiation factors are substances released by cells, which induce proliferation (growth factor) or differentiation (differentiation factor) in other cells (paracrine factors) or in the same cell (autocrine factors). These factors can be supplemented to the cell culture media if known.

Proliferation means increase in cell mass by repeated rounds of cell division.

Drugs are any chemical or biological substances, synthetic or non-synthetic, that when administered, will in some way alter the functions of that organism. Drugs are usually distinguished from endogenous biochemicals by being introduced from outside the organism.

Multi-parallel means separated culture compartments with identical cultures and culture conditions. The multi-parallel compartments are individually supplied with cell culture media and samples of each compartment can be drawn continuously. The compartments can preferably all be inspected individually using a microscope. The term multi-parallel comprises 2 to 200 individual, but identical culture settings.

Culture Device

The culture device may be plate-shaped. In a top view it may be rectangular or circular. Preferably it is rectangular. The culture device may be produced of any material compatible with cell culture, in particular, non-cytotoxic cell culture tested material. Examples for the material are plastic materials, e.g., thermoplastic or duroplastic materials. Examples of suitable materials are polyethylene, polypropylene, polysulfone, polycarbonate, polyetherethylketone (PEEK) or polytetrafluorethylene (PTFE). The culture device may be translucent. The culture device may be sterilized. The device may be produced by injection molding, notably if it is made of a thermoplastic material. Alternatively, it may be produced by compression molding, notably if it is made of a duroplastic material. In a further alternative, it may be assembled from individual layers.

The culture device comprises a plurality of culture units. The culture device may have 2 to 200 culture units, preferably, 6, 8, 12, 16 units, or multiples thereof. There are no particular limitations as to the arrangement of culture units, examples of possible arrangements are shown in FIG. 1 to 4. Each culture unit comprises a culture chamber, an inlet port and an outlet port.

In one embodiment, each culture unit has inlet and outlet ports separate from the inlet and outlet ports of other culture units on the device.

In another embodiment, two or more culture chambers may share the same inlet port, but have separate outlet ports. Sharing of inlet ports may be achieved by having multiple liquid conducts, each conduct connecting the inlet port with one culture chamber. This embodiment may be used for culturing cells under identical conditions in more than one culture chamber for testing reproducibility of an experiment. The ports of the culture units may be located in proximity to the culture chamber of the unit.

The culture chamber may be in a miniaturized format. In a top view the culture chamber may be rectangular or circular. The chambers may be formed by drilling. The chambers can be rectangular (5×5 mm to 25×25 mm or 10×10 mm with a height of 0.5 mm to 5 mm or 1 to 3 mm) or circular (diameter 6 mm to 20 mm or 8 to 14 mm with a height of 0.5 mm to 5 mm or 1 to 3 mm). The culture chamber may have a culture volume from 25 to 1000 µl, 50 to 250 µl, or 50 to 150 µl. The culture chamber may be reversibly closed on the top side by a lid. The lid may be a cover covering several culture chambers. Alternatively, individual culture chambers may be individually closed, e.g., by cover slides or by a polymer film.

The culture chamber may be translucent for allowing microscopic inspection of cells present in the culture chamber. The culture chamber may have a grooved or a flat bottom side. The latter is particularly suited for allowing microscopic inspection of cells present in the culture chamber.

The culture chamber is in fluid communication with an inlet port for connecting the culture unit to an external liquid supply. The culture units may be connected through the inlet port with a pump. The pump may be a peristaltic, membrane or syringe pump. In order to realise minimal continuous flow rates, syringe pumps (e.g. KD Scientific) may be the preferred type of pump.

The external liquid supply may be a culture media for the culture of eukaryotic cells. Fluid communication between the external liquid supply and the inlet port may be established by a conduct, such as a tubing. The conduct may be reversibly connected with the inlet port using standard fittings, as are generally used in the art. For example, Luer connectors or M6 connectors may be used as fittings. The inlet port is adapted for receiving the corresponding fitting of the conduct. For example, for a female fitting on the conduct, the inlet port has a corresponding male counterpart.

The outlet ports may be adapted for connection with a conduct, similarly as described for the inlet ports. A conduct connectable to the outlet port may lead to a waste container, a sample collector or analysis device, such as probes for pH and $pO_2$, microchips, biosensors, etc. Disposable probes for pH and $pO_2$ and biosensors can also be integrated into the culture chamber or the conduct connectable to the outlet port.

The culture chamber is in fluid communication with an inlet port and outlet port. The fluid communication between the culture chamber and the inlet port may be established by a channel connecting the culture chamber with the inlet port. The fluid communication between the culture chamber and the outlet port may be established by a channel connecting the culture chamber with the outlet port.

The channels may be formed by milling. The channels may be miniaturized, and may be adapted for the desired flow rate of culture media to the culture chamber. The channel may have a circular cross-section, the diameter of the cross-section may be between 0.1 mm and 3 mm, or 0.3 to 1 mm.

The inlet and outlet port and culture chamber of one culture unit may be arranged such as to allow liquid flow through the culture chamber, whereby the mainstream of the liquid flow traverses the culture chamber within the plane of the culture device, i.e. a plane parallel to the base plane of the culture device. The direction of the flow may be from the inlet port to the outlet port. Depending upon the position of the device, the flow may be in the horizontal or vertical direction.

The culture device of the invention has preferably overall a plate-like shape (e.g. as known from multi-well tissue culture plates) and has a plurality of identical units. Corresponding points in different culture chambers in a device having at least three culture chambers define the orientation of a plane referred to as base plane of the culture device. The mainstream of the liquid flow represents the overall direction of liquid flow between the openings of the culture chamber for afferent and efferent flow. Parallel means parallel or a deviation from parallel of at most 50%, 30%, or 20%. Ideally, the openings of the culture chamber for afferent and efferent flow are spaced apart, such that the fluid may penetrate the entire volume of the culture chamber before exiting the chamber. As exemplified in the figures the openings may be facing each other. Thereby, a nearly homogenous distribution of media components may be achieved in the culture chamber.

The flow rate of the liquid flow may be chosen as to suit the desired application and the inner volume of the culture chamber. The flow rate may be in the range of 10 to 1000 µl/day. Generally, the flow rate may be chosen such that the volume of the liquid that is passed through the culture chamber per day is between a quarter of the volume and four times the volume of the culture chamber. Preferably, 1 to 2 times the volume of the culture chamber is passed through the culture chamber per day. The culture chamber may be continuously perfused, which represents a constant perfusion with a continuous liquid flow or perfusion at predefined intervals, e.g., 1 µl every 15 min., or 1 µl every 30 min. A perfusion at predefined intervals may be realized by using, for example, a peristaltic pump or syringe pump. The flow rate may be constant or it may be varied during the period of incubating cells.

In one embodiment, the culture chambers are sealed on at least one side with a gas-permeable foil. In this embodiment, the cultured cells may be supplied with gas by equilibrating the culture media in the culture chamber to the predefined oxygen and carbon dioxide content of the environment, e.g., 20% oxygen, 5% carbon dioxide. The environment may be the air in the cell culture incubator. The gas-permeable foil may be manufactured from plastic films known to the person of skill in the art, which allow diffusion of oxygen and carbon dioxide from the surrounding atmosphere. For example, Biofoil25™ distributed by Greiner bio-one may be used.

In another embodiment, the culture chamber is gas-tightly closed except for openings involved in fluid communication of the culture chamber with the ports. Gas supply of the cells in the culture chamber may be achieved by pre-equilibrating the culture media before it passes into the culture chamber. For this purpose, the culture device may further comprise a conduct between the inlet port and the external liquid supply, the conduct comprising a gas permeable conduct that allows equilibrating liquid media to a predefined oxygen and carbon dioxide content (e.g. 20% oxygen, 5% carbon dioxide) of the environment, e.g. the air in the cell culture incubator. The gas permeable conduct may be manufactured from silicone.

Alternatively, the cell culture media may be pre-equilibrated to a predefined oxygen and carbon dioxide content with a percolator. For this purpose, the liquid reservoir of the liquid supply may be equipped with a percolator connected to an external gas supply (e.g. 20% oxygen, 5% carbon dioxide). With this embodiment, the culture device can be operated in a heating cabinet at 37° C.

In one embodiment, the culture device may be assembled from parts. One part may comprise a first plate-shaped plastic which has channels and culture wells in an arrangement that resembles the arrangement of channels and culture chamber of the culture units according to the invention. Channels and culture wells may be formed in the first plate-shaped plastic by milling or drilling. On top of the first plate-shaped plastic a cover may be installed, e.g. by mounting a second plate-shaped plastic, which may be adhered to the first plate (e.g. with dichloroethane). Ports may be mounted (e.g. with medical silicone adhesive) such that they are in fluid communication with the culture chamber.

In one embodiment the culture chamber may be perfused with liquid culture media and supplements. Media stands for liquids with nutrients and substances necessary for cultivation of cells. Liquid culture media for culturing eucaryotic cells are known to the person skilled in the art (e.g., DMEM, RPMI 1640, etc). Suitable media may be selected depending on the type of cells to be cultured. For example, lymphocytes may be cultivated in RPMI 1640 10% FCS. Lymphocytes may also be cultured using X-Vivo 15. Any suitable media may be chosen, however, it has to be assured that the measured lymphocyte response is not modified by factors in the media that are alien to the situation in the human body (e.g. plant-derived factors). Supplements describe substances to be added to culture media in order to induce or modify cell function (e.g. cytokines, growth and differentiation factors, mitogens, serum). Supplements are known to the person of skill in the art. One example of a serum commonly used with eukaryotic cells is fetal calf serum. The culture media may further be supplemented with antibiotics, such as penicillin, streptomycin, etc.

In one embodiment, test substances and/or stimulatory agents may be added to living cell material in each individual unit separately. Test substances may be pharmaceutical drugs or drug components. Stimulators may comprise any of the substances which support maintenance, growth or differentiation of cells. In a particular embodiment, stimulators are substances which act on immune cells, e.g. by activation of immune cells. Stimulators for activation of immune cells are known from the prior art. Such agents may be polypeptides, peptides or antibodies and other stimulators. For example, OKT-3, interferon-alpha, interferon-beta and interferon-gamma, oligoCPGs, mitogens (e.g. PWM, PHA, LPS), etc. Test substances and stimulators may be injected into the cell culture medium flow using a port in defined distance from the culture compartment or may be supplemented to the cell culture media reservoir and then being continuously supplied by the pump for the whole culture time or a predefined period of the culture time (e.g. the first 24 hrs).

In a further embodiment, the culture chamber may contain living eukaryotic cell material embedded in a matrix. Alternatively, eukaryotic cell material in the culture chamber may be seeded on a matrix already provided in the culture chamber.

Matrix describes substances or mixtures for surface coating or voluminous application to optimize cell attachment or allow 3D embedded culture. An optimal matrix would emulate the corresponding in vivo situation of the cells (e.g. promote cell proliferation, differentiation, function or tissue formation of cells, expression of cell-specific phenotypes and the activity of the cells). Matrices can include artificial or biogenic substances like hydrogels, sponges, foams, fabrics or non-woven fibres. The matrix may be selected from a hydrogels, sponges, foams, fabrics or non-woven fibres. Matrices are defined by structure, chemical composition and/or functionalisation, e.g., with extracellular matrix proteins. The structure of the matrix may allow optimal transfer of nutrients, supplements, test substances and gas to the cells.

Polymers may be formed from any suitable monomer known to the person of skill in the art. The polymer is biocompatible, either biodegradable or non-biodegradable. Acceptable polymers include agarose, collagen, fibrin, alginate, hyaluronic acid, chitosan, chitin, polytrimethylene carbonate, poly hydroxybutyrate, amino acid based polycarbonates, poly vinylchloride, polyvinyl alcohol, polymethacrylate, poly fumarate, polyHEMA, polystyrene, PTFE, polyethylene glycol, or polyethylene glycol based polymers and derivatives thereof. Biodegradable polymers include polylactides, glycolides, caprolactones, orthoesters and copolymers thereof.

For example, a hydrogel may be prepared using Matrigel™. Sponges may be out of collagen (OptiMaix™ form Matricel).

Foams for example may be made of polyethersulfone (GKSS) or polystyrene (Wilden AG). Non-woven fibres may be made of polyamide as used for preparation of erythrocyte concentrates for blood transfusion (Asahi) or manufactured using electro-spinning technology (J. H. Wenndorff).

The culture device may contain preformed solid matrices, especially foams (e.g. of polystyrene or polyethersulfone) or non-woven fibres (e.g. polyamide wool or electro-spun products) or sponges (e.g. Collagen or polystyrene).

The matrix may be perfused by liquid media, such that the liquid passes mainly through the interior of the matrix. The matrix may almost completely fill the inner volume of the culture chamber.

Living eukaryotic cell material may be embedded in the matrix by preparing a suspension of cells in an aqueous matrix-forming composition and solidifying the suspension. Hydrogel cell suspensions can either be solidified by decreasing the temperature (agarose) or rising the temperature of the matrix cell suspension to 37° C. (e.g. Matrigel™, collagen gel, fibrin gel).

In a preferred embodiment, living eukaryotic cell material may comprise immune cells. An example is leucocytes or co-cultures of leucocytes with other cells of interest. The leucocytes may be selected from the group consisting of whole peripheral blood mononuclear cells, defined subpopulations of peripheral blood mononuclear cells, in vitro differentiated peripheral blood mononuclear cell subpopulations and any co-cultures of these. The other cells of interest may be selected from the group consisting of endothelial cells, stem cells, follicular dendritic cells, stromal cells and others.

Furthermore cell lines with specific immunological properties may be cultured and examined in this culture system. These cells can be T cell lines (e.g. Jurkat), B cell lines (e.g. Ramos, Raji) or dendritic cell lines (e.g. Nemod) or mixtures thereof.

In one embodiment, culture units may comprise an additional inlet port for introducing a suspension comprising eukaryotic cells and/or an aqueous matrix-forming composition into the culture chamber. The inlet port for introducing the matrix forming composition may be connected with the culture chamber through a conduct, e.g. a matrix channel. One example of the embodiment is shown in FIG. 3. The matrix channel may be milled into the plate of the culture device, e.g, on the same side of the plate shaped culture device as the bottom side of the culture chamber. The culture chamber may be filled with a predefined volume of the suspension. For example, culture chamber may be filled through an opening in the bottom or bottom part of the lateral side of the culture chamber. Thereby, the risk of enclosing air bubbles in the matrix suspension in the chamber is minimized.

The suspension may be solidified inside the culture chamber using matrix-specific protocols. Alternatively, cells may be seeded onto a solid matrix preformed in the culture chamber. The solid matrix may comprise foams (e.g. of polystyrene or polyethersulfone), non-woven fibres (e.g. polyamide wool or electro-spun products) or sponges (e.g. collagen or polystyrene). Cells may be seeded onto the solid matrix through the inlet port or a separate port.

In another embodiment, culture units may further comprise hollow fibre membranes traversing the culture cavity. The hollow fibre membranes are in fluid communication with the culture chamber and the ports for allowing a liquid flow through the culture chamber. This embodiment is exemplified in FIG. 4. Liquid culture media and supplements may be passed into the culture chamber through a first hollow fibre and pass out of the culture chamber through a second hollow fibre. Suitable hollow fibre membranes may thus be manufactured from any material that is compatible with cell culture and allows the penetration of aqueous liquids, nutrients and supplements and other agents which are to be brought in contact with the cells. Suitable hollow fibre membranes are commercially available, e.g. MicroPES from Membrana. In a special embodiment, the culture chamber flanked by a first and a second hollow fibre membrane and a matrix channel is manufactured in a separate cassette as illustrated in FIG. 4B. This cassette can be manufactured by milling and drilling or by compression moulding. The membrane pieces are later on inserted and tightly joined to the cassette by applying pressure, heat or adhesives. The cassette can than be inserted into the baseplate comprising media channels, the venting channels and part of the matrix channels leading to the matrix port. The precisely tailored cassette is inserted into the baseplate by applying pressure or adhesives.

In a further embodiment, the hollow fibre membranes may be connected with an air outlet. Thereby, air may be removed from the hollow fibre membrane and/or culture unit.

Hollow fibres are filled with media by opening the inlet and outlet port, and if present, the air outlet port as well. Cell culture media is now pumped through the hollow fibre until it is filled with media and the air outlet ports are closed afterwards. Then, the pre-filled supply conduct (e.g., a tubing pre-filled with culture medium) and the efferent conduct can be connected to the inlet and outlet port, respectively.

In another aspect, the culture chamber may contain two compartments separated by a semi-permeable membrane, wherein one compartment is a compartment for living cell material in liquid media and the other compartment is a liquid media compartment that is perfused by the liquid flow. Thereby, aqueous liquids, nutrients and supplements and other agents which are to be brought in contact with the cells may penetrate into compartment for living cell material, and cellular products, e.g., waste, metabolites (e.g. glucose, lactate) and factors secreted from the cells, may be passed out of the compartment for living cell material, whereas living cell material is retained.

In one embodiment, the liquid media compartment of the culture chamber may be perfused by lateral flow, such that a fluid flow alongside the interface of the semi-permeable membrane with liquid media in the liquid media compartment is established.

Methods

In a further aspect, the invention provides methods of cultivating immune cells.

According to the methods of the invention, the individual culture units may provide comparable conditions. For example, a plurality of culture units may be treated identically, e.g., with regard to environmental factors such as temperature, gas, humidity and culture conditions, such as cell type, cell density, medium composition, supplements, matrices, flow rate of perfusion flow.

The matrices used with the methods of cultivating immune cells according to the invention may be a hydrogel, foam or non-woven fibre, which may be prepared as described above. In a preferred embodiment, the matrix is a hydrogel. The cells may embedded in a matrix such as a hydrogel by solidifying a suspension of cells in an aqueous matrix forming composition. The matrix may be solidified according to matrix specific protocols as described above. The matrix may be a 3-D matrix.

The matrix is solidified inside the culture chamber using known matrix specific protocols. Living eukaryotic cell material may be embedded in the matrix by preparing a suspension of cells in an aqueous matrix-forming composition and solidifying the suspension. Hydrogel cell suspensions can either be solidified by decreasing the temperature (agarose) or rising the temperature of the matrix cell suspension to 37° C. (e.g. Matrigel™, Collagen).

As described above, a suspension comprising immune cells may be introduced into the culture system of the invention via an inlet port associated with a culture chamber using standard methods, e.g., by injection.

The immune cells can be leucocytes or co-cultures of leucocytes with other cells of interest. The leucocytes may be selected from the group consisting of whole peripheral blood mononuclear cells, defined subpopulations of peripheral blood mononuclear cells, in vitro differentiated peripheral blood mononuclear cell subpopulations and any co-cultures of these. Leucocytes comprise defined subpopulations of leucocytes, such as lymphocytes (T cells, B cells) monocytes and in vitro differentiated leucocytes and any co-cultures of these (e.g., T cell and dendritic cell co-culture or B/T cell and dendritic cell co-cultures). Furthermore leucocytes or defined subpopulations of leucocytes may be co-cultivated with other cells of interest selected from the group consisting of endothelial cells, stem cells, follicular dendritic cells, stromal cells and others. In addition cell lines with specific immunofunctions can be used. These cell lines are derived from immune cells and can mimic immune responses. These cells can be selected from a group consisting of B cell lines (e.g. Ramos, Raji), T cell lines (e.g. Jurkat, Karpas-299) or dendritic cell lines (e.g. Nemod), or others known to the skilled person. Also mixtures of these cell lines can be cultured in this device.

A suitable ratio for the co-cultivation of in vitro generated dendritic cells (DCs) with PBMC may be a ratio of 1:10. PBMC may be co-cultured with follicular dendritic cells at a ratio from 1:10 to 1:50, stroma cells may be cultured with PBMC in a ratio from 1:10 to 1:100. Using B cell and T cell cultures, both subsets may be cultured in an equal ratio.

In one embodiment, the methods of cultivating immune cells may be used for long-term cultures, e.g., the immune cells may be incubated at predefined culture conditions for a period of time of several days, at least 1 week, at least 4 weeks and up to 8 weeks. The culture conditions and period of incubation depends on a number of factors, e.g. the type of cells cultivated and the type of immune answer to be detected.

The immune cells may be seeded at a high density, e.g. $1 \times 10^6$ to $1 \times 10^{10}$ viable cells per ml. Preferably, cells are seeded at a density of $1 \times 10^7$ to $5 \times 10^8$ viable cells per ml.

The culture conditions are defined by culture media, supplements, matrices, technically supported micro-environment and gas supply. Individual culture units may provide comparable conditions. The culture conditions may be chosen according to the type of cells. For example, cells may be incubated at 37° C., 5% $CO_2$ and 20% oxygen. The cultured cells may be provided with gas through a gas permeable membrane that seals at least one side of the culture chamber.

The matrix can be continuously perfused with fresh liquid media, whereby the medium which has passed through the culture chamber or is discharged at the outlet port is not recirculated.

In another embodiment, the matrix, culture media composition, cell density and cell mixture allow formation of microorganoid structures. Thereby, immune cells and co-cultures of the cells with other cells of interest may be cultivated to emulate tissue or organ function. According to the methods of the invention immune cells may establish cell-to-cell contacts and grow in microgradients/homeostasis and an architecture mimicking the relevant micro-environment for self-organisation of a specific tissue.

The culture system of the invention and corresponding methods of cultivating immune cells, e.g., leucocytes and co-cultures of leucocytes with other cells of interest allows emulating immunogenicity and immune functions in vitro.

The culture system of the invention allows mimicking immunological functions and testing immunogenicity in vitro and is aimed for testing the effects of substances as drugs and immunological stimulators on immune cells and co-cultures of immune cells and associated cells known to the specialist.

Another object of the invention is to provide a method of analysing the effect of a test compound on immune cells.

Immune cells may be of the type as described above. Immune cells are embedded in cell culture suitable matrices that may allow self-conditioning, building up of micro-environments and cell migration. The matrices may be 3D support structures that allow the cultivation of immune cells at high density (i.e. $1\times10^6$ to $1\times10^{10}$ viable cells per ml). The cells may be embedded in a matrix such as a hydrogel by solidifying a suspension of cells in an aqueous matrix forming composition. Alternatively, cells may be seeded on a sponge, foam or non-woven fibre matrix preformed in the culture chamber, by transfusing the matrix with a cell suspension such that cells are entrapped in the porous structure of the matrix.

When cells and matrix are filled into the system, the cell culture may be pre-incubated without a stimulus for 12 hours, 24 hours, or 48 hours or longer, or a time frame of 12-48 hours or 12-24 hours.

The incubation of immune cells embedded in a matrix may be performed as described above for the method of cultivating immune cells. The culture conditions and period of time for the incubation may be chosen according to the cell type and read-out parameter of the subsequent test. For example, for PBMC, a cytokine profile may be generated within 1 to 2 weeks, whereas the generation of an antibody response may take 2 to 21 days (IgM), or 4 to 21 days (IgG) and may continue up to 40 days. A T cell response may develop within 3 to 7 days. For specific proliferation, cells may be incubated between 2 to 21 days.

The culture system may be perfused for long-term cultivation of the cells, e.g., at least 1 week, up to 4 weeks and even up to 8 weeks.

During the incubation of immune cells in the methods of the invention, the culture chamber may be continuously perfused. For continuous perfusion syringe pumps, peristaltic pumps or membrane pumps may be used, whereby liquid media is either constantly, pumped into the culture chamber or at predefined intervals. With the use of a peristaltic pump, medium may be passed into the culture chamber at a rate of, e.g., 1 µl every 30 min, 1 µl every 45 min, 1 µl every 60 min, etc. The flow rate depends on a number of factors, e.g. the inner volume of the culture chamber, the density of cells, etc. Suitable ranges for the flow rate may be chosen as described above.

The test compound may be drugs or drug components of interest or stimulatory agents (e.g. stimulators) which influence (e.g. activate) cells or combinations of these. The test compound may be added to the medium that passes into the culture chamber, e.g. by injection into a septum.

The cells may be incubated with the test agent in a therapeutically effective dose and for a therapeutically effective time, which depends on the nature of the test compound.

The matrices used with the methods of analysing the effect of a test compound on immune cells according to the invention may be a hydrogel, foam or non-woven fibre, which may be prepared as described above. In a preferred embodiment, the matrix is a hydrogel.

In a preferred embodiment the matrix is continuously perfused with fresh liquid media, whereby the medium discharged at the outlet port is not recirculated. This set up is ideally suited for obtaining profiles of the generated response in a time-dependent manner, e.g., measuring an increase in cytokine secretion during the period of incubation. This protocol also offers optimal support of the cells with oxygen and nutrients to maintain high viability of the cells, thereby permitting long-term cultivation of the cells.

Samples of the culture media discharged at the outlet port may be taken by removing equal volumes of culture media at predefined intervals. The length of intervals depends on the read-out parameter. Samples may be taken every 1 hour to 3 days, preferably every 6 hours to 1 day.

In a further aspect, in step e) of the method of analysing the effect of a test compound on immune cells, the presence or concentration of soluble factors selected from cytokines, chemokines and antibodies are analysed in the sample. The soluble factors may be proteinaceous substances secreted by the cells (e.g. IL-2/4/5/10, TNF-alpha and IFN-gamma, MIP1alpha or antibodies).

In a preferred embodiment, the sample is removed while maintaining incubation of the cells. This allows to improve reproducibility of the measurement. In a further aspect, this embodiment allows to generate data in a time-dependent manner, e.g., profiling the rise of cytokine content in the afferent fluid, as it is secreted by the cells.

In another embodiment, the test compound, concentration of test compound, time of exposing the cells to the test compound are different between individual culture units. Thereby, tests of high statistical relevance and reproducibility may be carried out.

In another embodiment, the method of analysing the effect of a test compound on immune cells further comprises online monitoring and/or offline monitoring of cell culture conditions in culture media discharged at the outlet port.

Online monitoring may be carried out using biosensors and biosensor methodology known to the person skilled in the art. Read-out parameters for online monitoring comprise pH, oxygen content, nutrients and metabolites, such as, e.g., glucose, lactate. Factors secreted from the cells, such as cytokines, chemokines, antibodies and metabolites of the cells may be further analysed by removing samples from the culture media discharged at the outlet port and analysing the sample by off-line measurements. Methods for off-line analysis may be, e.g., ELISA, Biacore SPR technology or multiplex bead array technology.

For example, cytokine profile may be generated using multiplex bead array technology (Luminex™/Luminex Corporation, Flow Cytomix™/Bender Medsystems or CBA/BD), where cytokines bind to specific, fluorescent beads and are subsequently quantified by FACS analyses. Which cytokines are included in the test depends on the commercially available multiplex kit chosen.

At the end of the culture, the matrix-embedded cells can be inspected using a variety of methods by opening the culture compartment. The cell matrix construct from the culture compartment can either be directly embedded in paraffin and dissected for histological analyses or the matrix is enzymatically digested (e.g. collagenase, plasmin) in order to get single cells for further analyses.

In a further aspect, the method of analysing the effect of a test compound on immune cells may further comprise analysis of the immune cells by a method selected from the group of light microscopy, histology, immune fluorescence techniques, flow cytometry, fluorescent activated cell sorting (FACS), enzyme linked immuno-spot technique (ELISPOT), molecular biology techniques (e.g. DNA, RNA chips) and others known to the skilled person.

Detailed Description of the Figures

FIG. 1: Top view (FIG. 1A) and cross cut of one culture unit (FIG. 1B) of device 1. The multi-parallel culture units consist of media channels (4) and culture compartments (2) which are milled in a plastic baseplate (e.g. polycarbonate; 6). The culture compartments of this embodiment have a diameter of 10 mm and a height of 1 mm (79 μL). The baseplate is sealed with a gas permeable foil (biofoil25; 5) for optimal gas supply (oxygen, carbon dioxide) of the cultures. The gas permeable foil is bonded to the baseplate (e.g. with medical pressure sensitive silicone adhesive). On top of the baseplate a second plate (7) covers culture compartment and channels. The cover plate is bonded to the baseplate (e.g. with dichloroethane). Luer ports (1 and 3) are mounted (e.g. with medical silicon adhesive) to the baseplate and allow the connection of the peripheral fluidic system to the inlet and outlet channels. The system is inoculated via the inlet port (1) with matrix-cell suspension. After the matrix is gelled, the peripheral fluidic system is connected to ports and the culture compartment is continuously perfused with cell culture media and supplements. The samples are collected via the outlet media ports (3) for further analyses.

FIG. 2: Top view (FIG. 2A) and cross cut of one culture unit (FIG. 2B) of device 2. Analogous to device 1 multi-parallel culture units are realised on a baseplate (6) covered with a cover plate (7) and sealed with a gas permeable foil (5) at the bottom. A larger culture compartment with 10 mm in diameter and 4 mm in height is realised on this plate.

FIG. 3: Top view (FIG. 3A) and cross cut of one culture unit (FIG. 3B) of device 3. Analogous to device 1 and 2 multi-parallel culture units are realised on a baseplate (6) covered with a cover plate (7) and sealed with a gas permeable foil (5) at the bottom. In this embodiment of the invention, the culture compartment is filled with matrix-cell suspension via a separate port (8) and matrix-channel (9). The culture compartment (2) of this embodiment has a diameter of 10 mm and a height of 4 mm. When inoculated, the culture compartment is filled with matrix-cell suspension via the matrix port (8) using a syringe. After the filling, the matrix port is closed with a blind luer adapter. When the matrix is gelled, the peripheral fluidic is connected to the media supply (1) and probe sampling port (3) and the culture compartments are continuously perfused with cell culture media and supplements, which enter the culture chamber through media channels (4).

FIG. 4: Top view (FIG. 4A) and 3D projection of a part of one culture unit (FIG. 4B) of device 4. Analogous to devices 1 to 3, multi-parallelculture units are realised on a baseplate (6) covered with a cover plate (7) and sealed with a gas permeable foil (5) at the bottom. In this embodiment of the invention, the cell culture media and supplement are delivered to the culture chamber through a hollow fibre membrane (e.g. MicroPES, Membrana, outer diameter 2 mm; (10)). In this embodiment of the invention, the hollow fibre membranes are mounted in a separate cassette comprising the culture chamber. This cassette is inserted into the baseplate such that media channels, the matrix channel and venting channels are each properly connected. When inoculated, the culture compartment is filled via the matrix port (8) and matrix channel (9) with cell/matrix-cell suspension. After the matrix port is closed, the controlled gelling of the matrix can be induced by a temperature shift. The peripheral fluidic conducts are connected to the inlet and outlet ports. The first and the second hollow fibre membranes are each filled with media by pumping media into the system while the ports for air outlets (11) are open. Using this protocol, perturbing air bubbles in the fluidic system are avoided. The air outlet ports are closed after filling the system with cell culture media and the incoming cell culture media can now perfuse the culture compartment homogeneously. After perfusing the culture compartment, the media passes through a second hollow fibre membrane which retains matrix and cells and is drained via the port for probe sampling and collected in an individual probe sampling container.

Legend FIG. 1 to 4
1—port for media supply (inlet)
2—culture compartment
3—port for probe sampling (outlet)
4—media channel
5—gas permeable foil for gas supply of the culture
6—baseplate with channels and culture compartments
7—cover plate
8—port for filling the culture compartment with matrix-cell suspension
9—channel for filling the culture compartment with matrix-cell suspension
10—hollow fibre for media supply and probe sampling
11—ports for air outlet while filling the system with media FIG. 5: Cytokine profile of multi-parallel PBMC cultures in device 1 according to example 1. The data was generated using multiplex bead array technology (Luminex, Austin, Tex.). TNF-alpha, IL-5, IL-4, IL-2 and IFN-gamma are included in this test. 24 hours after inoculation 100 μL of a 100 ng/mL OKT-3 solution was injected into the culture system eliciting a specific immune reaction.

FIG. 6: Cytokine profile of multi-parallel PBMC cultures in device 1 according to example 2. The data was generated using multiplex bead array technology (Luminex, Austin, Tex). TNF-alpha, IL-5, IL-4, IL-2 and IFN-gamma are included in this test. 24 hours after inoculation 100 μL of a 100 ng/mL OKT-3 solution was injected into the culture system eliciting a specific immune reaction.

FIG. 7: Experimental set-up of one exemplary culture unit and the corresponding peripheral fluidic system. The cooled media reservoir (A) contains cell culture media and supplements. The reservoir is connected with a media pump (B), e.g., a peristaltic pump or syringe pump. The tubing goes into the incubator and is connected to the port for media supply (C). Just before this port, an injection site (G), e.g., a septum allows the administration of drugs, stimulators or other compounds of immunological relevance. The cells are cultured and perfused in the culture compartment (D). Exhaust media is drained via the port for probe sampling (E) and collected in a sample container (F). The system allows the simultaneous handling of multi-parallel culture units with individual peripheral fluidic systems. Each cell culture media perfused unit generates an individual sample for further analyses.

Legend to FIG. 7
A—cell culture media reservoir (preferably at 4° C.)
B—media pump
C—port for media supply (inlet)
D—cell culture compartment of the device
E—port for probe sampling (outlet)
F—individual probe sampling container
G—injection site for administering drugs, stimulators or other immunological active substances FIG. 8: Glucose and lactate profile of PBMC cultures in device 4 according to example 4. The data points indicate the concentration of these metabolic parameters in the flow through in a time dependent manner. The flow through was analysed with an Ektachem system (Johnson & Johnson). Increased metabolic activity of OKT-3 and interleukin-2 stimulated cultures can be seen by reduced glucose and increased lactate concentrations in the flow through as compared to control cultures without OKT-3 and IL-2 stimulation.

Figure 9:
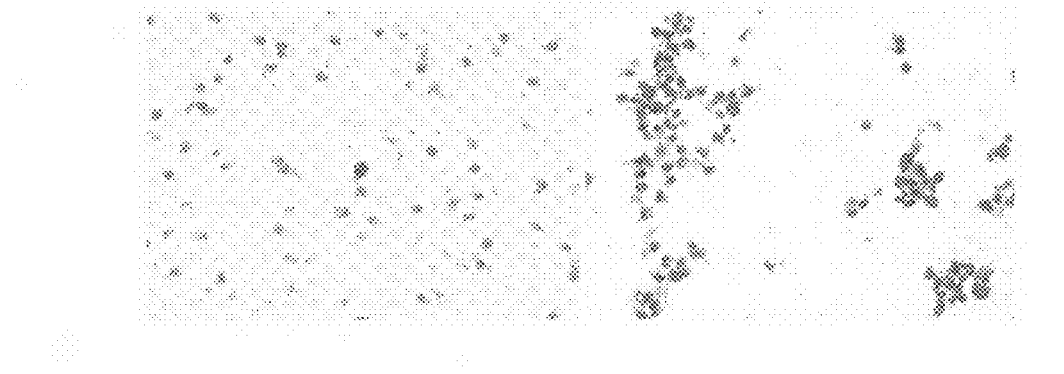
FIG. 9 shows immune histological sections specifically stained with anti-Ki67 antibody and counterstained with heamatoxiline, of a control (left) and a OKT-3 and IL-2 stimulated PBMC culture (right) in agarose matrix according to example 4.

FIG. 9: Immune histological sections specifically stained with anti-Ki67 antibody and counterstained with hematoxilin, of a control (left) and a OKT-3 and IL-2 stimulated PBMC culture (right) in agarose matrix. The cell matrix cultures were analysed after 7 days in culture according to example 4 (device 4). The control section shows less Ki67 positive cells (black) as compared to the control culture indicating T cell activation and induced proliferation in the stimulated culture.

Figure 10:
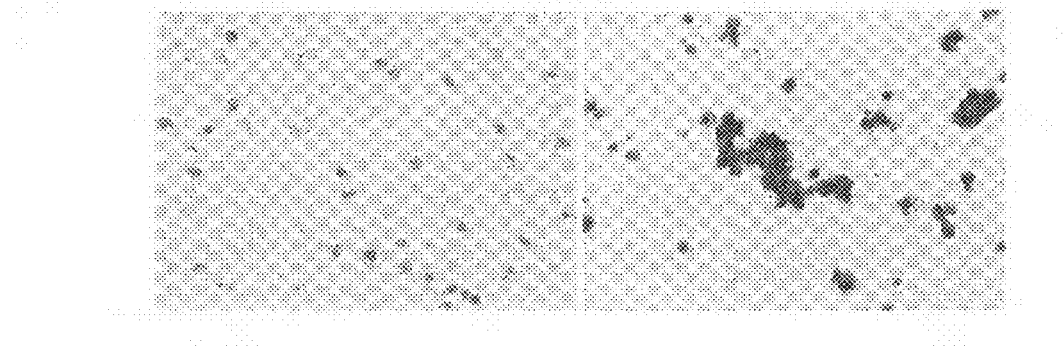
FIG. 10 shows immune histological sections specifically stained with anti-CD3 antibody and counterstained with heamatoxiline, of a control (left) and a OKT-3 and interleukin-2 stimulated PBMC culture (right) in agarose matrix according to example 4.

FIG. 10: Immune histological sections specifically stained with anti-CD3 antibody and counterstained with hematoxilin, of a control (left) and a OKT-3 and interleukin-2 stimulated PBMC culture (right) in agarose matrix. The cell matrix cultures were analysed after 7 days in culture according to example 4 using an embodiment of device 4 (see FIG. 4/4B). The control section shows less CD3 positive cells (black) as compared to the stimulated culture indicating induced T cell proliferation.

EXAMPLES

The invention will be further illustrated by the following non-limiting examples.
Abbreviations:
PBMC—peripheral blood mononuclear cells
FCS—fetal calf serum
° C.—degree centigrade
g, mg, µg—gram, milligram, microgram
L, mL, µL, nL—liter, milliliter, microliter, nanoliter
mm—millimeter
PC—polycarbonate
h, min—hour, minute
IL—interleukin
TNF-alpha—tumor necrosis factor alpha
IFN-gamma—interferon-gamma Example 1

Cryopreserved human PBMC, isolated from whole blood by ficoll density gradient centrifugation, were revitalised using standard protocols. The cell concentration was adjusted to 3 E8 viable cells per mL in X-Vivo 15 cell culture media (Lonza, Basel, Switzerland) supplemented with 5 mg/mL agarose type VII (made from 50 mg/mL 37° C. liquid solution, Sigma-Aldrich, St. Louis, Mo.), 2.5 µg/mL fibronectin (human, Sigma-Aldrich, St. Louis, Mo.) and 1× penicillin/streptomycin solution (100×, Invitrogen, Carlsbad, Calif.).

The device was made of a 1 mm PC plate housing the culture compartment, feeding and draining canals (see FIGS. 1 and 1A). The plate was covered with a 1 mm PC plate on top were the luer connectors were attached and a gas permeable membrane (Biofoil25, Greiner bio-one, Kremsmünster, Germany) at the bottom of the plate for optimal gas supply of the culture. The culture compartment of this special embodiment of device 1 has a volume of 160 µL. The device was incubated in a humidified incubator (37° C./5% carbon dioxide).

Three culture compartments of the device, further illustrated in FIG. 1A, were filled with cell suspension in liquid agarose media avoiding air bubbles (4,8 E7 viable PBMC/compartment). The whole culture device was cooled down to 4° C. for 5 min in order to let the matrix gel. Subsequently the surrounding fluidic system was prefilled with X-Vivo 15 cell culture media and was applied to the luer connectors of the culture device. A flow rate of 13.1 µL/h was set up using a peristaltic media pump.

Samples were taken every day and immediately frozen down to −20° C. for subsequent cytokine analyses using multiplex bead array technology (Luminex, Austin, Tex.).

After the second sample was taken 24 hours after innoculation, 100 µL OKT-3 antibody (100 ng/mL solution in X-Vivo 15, Ortho Biotech, Bridgewater, N.J.) were administered via an injection site in the fluidic system. 5 days after inoculation the last sample was taken and viability of the cultures was checked with acridine orange (1 µg/mL, Sigma, St. Louis, Mich.) and ethidium bromide (4 µg/mL, Sigma, St. Louis, Mich.).

The results of the cytokine analyses are displayed in FIG. 5. The point at t=0 h represents the cytokine concentration in X-Vivo 15 cell culture medium only. 24 hours after inoculation of the culture system, only low cytokine levels were observed, verifying that matrix and system have no stimulating effects. Another 24 hours after the OKT-3 administration, a massive IL-2 burst is observable. The OKT-2 antibody binds specifically to the eta-chain of the CD3 receptor on T cells. These, thereby activated T cells, start to release cytokines, particularly IL-2. Also pro-inflammatory cytokines such as IFN-gamma and TNF-alpha are released. The in vitro system emulates hereby pharmaceutical effects and common adverse effects when OKT-3 is administered in humans. After the initial burst of IL-2 production, the level declined after 72 hours. The matrix-assisted cultures showed high viability after 5 days in the system as analysed by acridine orange and ethidium bromide staining. The culture system and method thereby allows to examine immuno function stimulation of human PBMCs and immunological effects in a time dependent manner, while optimal support of the cells with oxygen and nutrients permits to maintain high viability.

Example 2

The experiment was conducted as described in example 1. PBMCs were derived from a differed donor and cells were subsequently cultured in RPMI 1640 (Invitrogen, Carlsbad, Calif.) supplemented with 10% FCS (Biochrom, Berlin, Germany) and 1× penicillin/streptomycin solution (100×, Invitrogen, Carlsbad, Calif.). As described previously, the culture compartment of culture device 1 (see FIGS. 1 and 1A) was filled with liquid agarose-media (RPMI 1640 10% FCS cell culture media supplemented with 5 mg/mL agarose type VII (from 50 mg/mL 37° C. liquid solution, Sigma-Aldrich, St. Louis, Mo.), 2.5 µg/mL fibronectin (human, Sigma-Aldrich, St. Louis, Mo.) and 1× penicillin/streptomycin solution (100×, Invitrogen, Carlsbad, Calif.) and cells (4,8 E7 PBMC/compartment). After pre-incubation for 24 hours with a constant perfusion rate of 13.1 µL culture media, 100 µL of a 100 ng/mL OKT-3 solution was administered. Samples were taken every 24 hours and frozen down to −20° C. before the cytokine levels were determined.

The cytokine profile (FIG. 6) of these experimental samples is comparable to the results obtained in experiment one. Again, the OKT-3 administration results in a massive IL-2 release and IL-5 also raises initially analogous to example 1. The pro-inflammatory cytokines IFN-gamma and TNF-alpha only raise slightly demonstrating donor specific differences. Also the height of the cytokine levels can be attributed to differences in cellular material and differences in media formulation between X-Vivo 15 and RPMI 1640 10% FCS. Comparable to example 1, immuno functional effects of the OKT-3 stimulation could be illustrated in a time-dependent manner.

Example 3

This special embodiment of culture device as illustrated in FIGS. 4 and 4B had a culture compartment of 3 mm×7 mm×7 mm and consequently a culture volume of 147 µL. The first and second hollow fibre membranes (inner diameter 1.5 mm/outer diameter 2.0 mm/Micro PES capillary membrane/ Membrana, Wuppertal, Germany) were inserted into the 3 mm polycarbonate baseplate in a separate cassette as illustrated in FIG. 4B. The first hollow fibre membrane was connected to channels leading to an inlet port and a venting port. The second hollow fibre membrane was connected to channels leading to an outlet port and a venting port The outlet port was connected via a conduct with a sample collection vial. The culture compartment was connected to a matrix port allowing liquid, gel-forming matrix to be filled in. The culture compartment and the channels for venting, media supply and probe sampling were covered with a 1 mm polycarbonate plate with all the luer ports for connecting to tubings on the top and a gas permeable foil (Biofoil25, Greiner bio-one, Frickenhausen, Germany) at the bottom. The 3 mm baseplate and the 1 mm cover plate as well as the 3 mm baseplate and the gas permeable foil were joined together with a pressure sensitive silicon adhesive (M7-4502, Dow Corning, Midland, USA). Like in other embodiments of the invention, 6 multi-parallel culture compartments were realised on one baseplate with outer dimensions corresponding to a multiwell plate.

Ramos cells (5 E5 viable cells/human Burkitt's Lymphoma/CD20 positive and CD3 negative) and Jurkat cells (1 E6 viable cells/human leukaemic T cell lymphoblast/CD3 positive and CD20 negative) cultured in RPMI 1640 (Invitrogen, Carlsbad, USA) +10% FCS (Biochrom, Berlin, Germany) were mixed in order to produce a co-culture of these cells and spun down at 200×g for 5 min. The cell pellet was resuspended in 100 μL RPMI 1640+10% FCS and mixed with 856 μL fibrinogen (3.5 mg/mL/Sigma-Aldrich, St. Louise, USA), 7 μL aprotinin (5 mg/mL, Sigma-Aldrich) and 25 μL thrombin solution (50 U/mL, Sigma-Aldrich). The inlet and outlet ports were opened, two culture compartments were quickly filled with cell matrix solution using a 1 mL syringe and the fibrin gel polymerised for 10 min at 37° C. The matrix ports were closed after gelling. The inlet port of each culture compartment was connected with a tubing to a media supplying 5 mL syringe (RPMI 1640+10% FCS+35 μg/mL aprotinin) and each of the outlet ports was connected via a tubing to a sample collection vial. In each culture compartment the first hollow fibre was flushed with cell culture medium with the venting ports open and a syringe connected for collecting the excessive medium. The second hollow fibres were each flushed using a syringe connected to the outlet venting ports and excessive media was collected in the corresponding sample vial. The syringes connected to the venting ports were taken off and the ports were closed. The sample vial was exchanged. The media supply syringes connected to the inlet ports were inserted into a syringe pump (KDS 220, KDScientific, Holliston, USA). The reactor was transferred into an incubator (37° C., 5% $CO_2$) and the perfusion pump was started with a continuous flow rate of 25 μL/hr.

After one day in culture one compartment was opened by cutting off the gas permeable foil at the bottom of the device using a scalpel and the cell matrix block was removed into a reaction tube. The gel was cut into pieces and incubated for 1 hr with 250 μg plasmin (Sigma-Aldrich) at 37° C. After the gel was digested enzymatically, cells were spun down and the pellet stained with 20 μL anti-CD3 APC-conjugated (BD, San Jose, USA) and 20 μL anti-CD20 FITC-conjugated (BD) antibodies and analysed by flow cytometry using a Partec CyFlow space (Münster, Germany). The procedure was repeated analogous after 5 days in culture. While at day 1 36% of the CD3-CD20 positive cells were CD20 positive (Ramos) and 64% were positive for CD3 (Jurkat) on day 5 in culture 91% were positive for CD20 and 9% were positive for CD3. Therefore, the culture device allows for endpoint flow cytometric analysis of cultured cells.

Example 4

In the following example a device analogous to the one described in example 3 was used. Again, culture compartments with the dimensions 3×7×7 mm were realised on the plate.

Cryopreserved human PBMC, separated from leucapheresis material applying density gradient centrifugation, were revitalised and pre-cultured overnight in a standard T-flask in RPMI 1640 (Invitrogen, Carlsbad, USA) 10% FCS (Biochrom, Berlin, Germany). On the day of inoculation, PBMC were harvested and 1 E8 cells were cultivated and stimulated in 10 mL RPMI 1640+10% FCS+100 U/mL Proleukin S® (Aldesleukin, Novartis, Basel, Schweiz)+50 ng/mL OKT-3® (Muromonab-CD3, Ortho Biotech, Neuss, Germany) for 2 hrs at 37° C. The control was incubated for 2 hrs at 37° C. in 10 mL RPMI 1640+10% FCS only. The PBMC were washed twice with cell culture media and resuspended in 750 μL RPMI 1640+10% FCS+100 U/mL Proleukin S® and 750 μL RPMI 1640+10% FCS (control) mixed with 250 μL pre warmed 20 mg/mL low-gelling agarose type VII (Sigma-Aldrich) in phosphate buffered saline. The cell matrix suspension was injected as described in example 3 and gelled at 4-8° C. for 10 min. The tubings were connected and the hollow fibre membranes were flushed as described in example 3. Media perfusion with RPMI 1640+10% FCS+100 U/mL Proleukin S® and RPMI 1640+10% FCS+(control) was started with 25 μL/hr.

The perfused culture medium was harvested on day 1, 2, 5, 6 and 7 and subsequently analysed for the metabolic parameters glucose and lactate (Ektachem, Johnson&Johnson, Langhorne, USA). On day 7 the cell matrix culture was prepared for histological analyses by fixation in 4% formaldehyde solution (Merck KGaA, Darmstadt, Germany) in phosphate buffered saline and fixed for 2 hrs. Subsequently, the specimens were dehydrated in an increasing alcohol row consisting of 80% ethanol, 96% ethanol and 100% iso-propanol for 20 min each. After dehydration, the matrix was transferred into histology cassettes, bathed in xylol for 2×10 min and embedded in paraffin (Carl Roth GmbH & Co, Karlsruhe, Germany; 65° C.) for 2 hrs. Specimen were stored at −20° C. until 7 μm slides were prepared and dried over night on SuperfrostPlus object slides (Menzel GmbH, Braunschweig, Germany). For deparaffinising, the slides were incubated for 2×5 min in xylol and subsequently rehydrated in a sequence of iso-propanol, 100% ethanol, 96% ethanol, 70% ethanol (3 min each) and purified water (10 min).

For immune histochemical staining, the sections were demasked with 1× target retrieval solution (DAKO, Hamburg, Germany) in purified water for 20-30 min at 95-99° C. and subsequently slowly cooled down for 20-30 min. After washing the slides with PBS for 10 min blocking with PBS 2% FCS for 15 min followed. The slides were incubated with primary mouse anti-human CD3 (BD, San Jose, USA) and anti-Ki67 (Biotrend, Cologne, Germany) antibody overnight and subsequently incubated with biotin conjugated anti-mouse secondary antibody (Dianova, Hamburg, Germany) and alkaline phosphatase conjugated extravidin (Sigma-Aldrich) for 45 min each, comprising a washing step (PBS) after each incubation. Visualisation was achieved by incubation with Sigma Fast Red (Sigma-Aldrich) for 5-15 min followed by a washing step with purified water. Slides were then counterstained with haematoxylin for 1-5 min, shortly rinsed with purified water and developed with tap water (10 min) before mounted in Kaiser's Glycerine Gelatine and examined under the microscope (bright field).

OKT-3 is a murine IgG2a monoclonal antibody recognizing the human CD3 eta chain of the T cell receptor. This antibody can induce T cell proliferation when used in low dose concentrations together with interleukin-2. Daily samples of the perfused culture medium were analysed for the metabolic parameters glucose and lactate. Comparing the results for the control and OKT-3/IL-2 stimulated cultures, increased metabolic activity was detected (see FIG. 8). The immune histological staining of sections shows higher Ki67 expression in OKT-3/IL-2 stimulated cultures confirming the metabolic data (see FIG. 9). Also proliferation of CD3 positive cells (T cells) was induced and T cell clones were detected after 7 days in culture when comparing anti-CD3 stained sections of the OKT-3/IL-2 stimulated culture with the control culture (see FIG. 10). This example illustrates that the analyses of the perfused culture medium as well as immune histological endpoint analyses of the cell matrix cultures allows comprehensive mode of action analyses of cellular responses in vitro. These cellular responses are induced by a specific micro-environment in the culture. Surprisingly, this micro-environment allows cellular responses comparable to those in vivo. This specific micro-environment is for instance realised by the present culture device.

Obviously, numerous modifications and variations of the present invention are possible in light of the above teachings. It is therefore to be understood that within the scope of the appended claims, the invention may be practiced otherwise than as specifically described herein.

The invention claimed is:

1. A method of analysing the effect of a test compound on immune cells, which comprises the steps of:
   (a) incubating immune cells embedded in a matrix in a culture chamber of at least one culture unit of a culture device, at predefined culture conditions for a predefined period of time, whereby the matrix is continuously perfused with liquid culture media and supplements,
   (b) adding the test compound to at least one culture unit through an inlet port,
   (c) incubating immune cells as described in step a) in the presence of the at least one test compound,
   (d) removing at least one sample of the culture media discharged from an outlet port of the at least one culture unit to which the test compound was added, and
   (e) analysing the sample for an effect of the test compound on the immune cells,
   wherein the culture device comprises a top side, a bottom side, and at least one lateral side, comprising a plurality of culture units, wherein each unit comprises:
      (i) a culture chamber,
      (ii) an inlet port for reversibly connecting the unit with an external liquid supply, and
      (iii) an outlet port for discharging liquid from the unit,
   wherein the inlet port is in fluid communication with the culture chamber and the culture chamber is in fluid communication with the outlet port for allowing a liquid flow through the culture chamber and the main stream of the liquid flow traverses the culture chamber within the plane of the culture device, and
   wherein the inlet port is accessible for connecting an external liquid supply from the top side or lateral side of the culture device, and the outlet port is accessible for connecting a discharge conduct from the top side or lateral side of the device.

2. The method according to claim 1, wherein the matrix is selected from a hydrogel, foam, sponge or non-woven fibres.

3. The method according to claim 1, wherein:
   (a) the sample is removed while maintaining incubation of the cells;
   (b) in step e) the presence or concentration of soluble factors selected from cytokines, chemokines and antibodies are analysed in the sample;
   (c) the test compound, concentration of test compound, time of exposing the cells to the test compound are different between individual culture units;
   (d) further comprising analysis of the immune cells by a method selected from the group of immune fluorescence, light microscopy, flow cytometry, fluorescence activated cell sorting, histology, molecular biology techniques and enzyme linked immuno-spot methods after the culture process; or
   (e) any combination thereof.

4. The method of claim 1, wherein in the culture device the fluid communication is established by a channel between the culture chamber and the inlet port and a channel between the culture chamber and the outlet port.

5. The method of claim 1, wherein the culture chamber or chambers:
   (a) are sealed on at least one side with a gas-permeable foil;
   (b) are gas-tightly closed except for openings involved in fluid communication of the culture chamber with the ports;
   (c) have a culture volume from 25 to 1000 µl;
   (d) are translucent for allowing microscopic inspection of cells present in the culture chambers; or
   (h) any combination thereof.

6. A method of analysing the effect of a test compound on immune cells, which comprises the steps of:
   (a) incubating immune cells embedded in a matrix in a culture chamber of at least one culture unit of a culture device, at predefined culture conditions for a predefined period of time, whereby the matrix is continuously perfused with liquid culture media and supplements,
   (b) adding the test compound to at least one culture unit through an inlet port,
   (c) incubating immune cells as described in step a) in the presence of the at least one test compound,
   (d) removing at least one sample of the culture media discharged from an outlet port of the at least one culture unit to which the test compound was added, and
   (e) analysing the sample for an effect of the test compound on the immune cells,
   wherein the culture device comprises a top side, a bottom side, and at least one lateral side comprising a plurality of culture wherein each unit comprises:
      (i) a culture chamber,
      (ii) an inlet port for reversibly connecting the unit with an external liquid supply, and
      (iii) an outlet port for discharging liquid from the unit,
   wherein the inlet port is in fluid communication with the culture chamber and the culture chamber is in fluid communication with the outlet port for allowing a liquid flow through the culture chamber, and
   wherein the inlet port is accessible for connecting an external liquid supply from the top side or lateral side of the culture device, and the outlet port is accessible for connecting a discharge conduct from the top side or lateral side of the device, and
   wherein the culture device further comprises a conduct between the inlet port and the external liquid supply, the conduct comprising a gas permeable conduct that allows equilibrating liquid media to a predefined oxygen and carbon dioxide content.

7. The method of claim 1, wherein the culture chamber of the culture device has a culture volume from 50 to 250 µl or from 50 to 100 µl.

8. The method of claim 1, wherein the culture device comprises 2 to 200 culture units.

9. The method of claim 1, wherein in the culture device the test compound is separately added to the immune cells in each individual unit.

10. The method of claim 5, wherein in the culture device the matrix is selected from a hydrogel, foam or non-woven fibres.

11. The method of claim 5, wherein in the culture device the immune cells comprise leucocytes or co-cultures of leucocytes with other cells of interest.

12. The method of claim 11, wherein in the culture device the leucocytes are whole peripheral blood mononuclear cells, defined subpopulations of peripheral blood mononuclear cells, in vitro differentiated peripheral blood mononuclear cell subpopulations, or any co-cultures of these.

13. The method of claim 11, wherein the other cells of interest are selected from the group consisting of endothelial cells, stem cells, follicular dendritic cells, stromal cells and others.

14. The method of claim 1, wherein in the culture device:
(a) the culture unit comprises an additional inlet port for introducing a suspension comprising eukaryotic cells and/or an aqueous matrix-forming composition into the culture chamber;
(b) the culture units further comprise hollow fibre membranes traversing the culture cavity, whereby the hollow fibre membranes are in fluid communication with the culture chamber and the ports for allowing a liquid flow through the culture chamber; or
(c) any combination thereof.

15. The method of claim 14, wherein the culture chamber, flanked by a first and a second hollow fibre membrane and a matrix channel, is manufactured in a separate cassette that can be inserted into a base plate comprising a media channel, a venting channel and part of the matrix channel leading to a matrix port, and wherein the hollow fibre membranes are mounted in the separate cassette comprising the culture chamber.

16. The method of claim 1, wherein the culture device provides a microenvironment.

17. A method of analysing the effect of a test compound on immune cells, which comprises the steps of:
(a) incubating immune cells embedded in a matrix in a culture chamber of at least one culture unit of a culture device, at predefined culture conditions for a predefined period of time, whereby the matrix is continuously perfused with liquid culture media and supplements,
(b) adding the test compound to at least one culture unit through an inlet port,
(c) incubating immune cells as described in step a) in the presence of the at least one test compound,
(d) removing at least one sample of the culture media discharged from an outlet port of the at least one culture unit to which the test compound was added, and
(e) analysing the sample for an effect of the test compound on the immune cells,
wherein the culture device comprises a top side, a bottom side, and at least one lateral side, comprising a plurality of culture units, wherein each unit comprises:
   (i) a culture chamber,
   (ii) an inlet port for reversibly connecting the unit with an external liquid supply, and
   (iii) an outlet port for discharging liquid from the unit,
wherein the inlet port is in fluid communication with the culture chamber and the culture chamber is in fluid communication with the outlet port for allowing a liquid flow through the culture chamber, and
wherein the inlet port is accessible for connecting an external liquid supply from the top side or lateral side of the culture device, and the outlet port is accessible for connecting a discharge conduct from the top side or lateral side of the device, and
wherein the immune cells embedded in the matrix are obtained by: (a) introducing a suspension of immune cells in an aqueous matrix-forming composition into the culture chamber, and (b) solidifying the suspension, thereby forming the immune cells embedded in the matrix, and wherein the suspension comprises non-adherent cells.

* * * * *